United States Patent
Jia et al.

(10) Patent No.: US 9,652,872 B2
(45) Date of Patent: May 16, 2017

(54) SYSTEM AND METHOD OF MEDICAL IMAGING

(71) Applicant: GE MEDICAL SYSTEMS GLOBAL TECHNOLOGY COMPANY, LLC., Waukesha, WI (US)

(72) Inventors: Lei Jia, Beijing (CN); Zhihui Sun, Beijing (CN); Bin Yang, Beijing (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/693,079

(22) Filed: Apr. 22, 2015

(65) Prior Publication Data

US 2015/0310638 A1    Oct. 29, 2015

(30) Foreign Application Priority Data

Apr. 23, 2014    (CN) .......................... 2014 1 0166402

(51) Int. Cl.
| | | |
|---|---|---|
| G06K 9/00 | (2006.01) | |
| G06T 11/00 | (2006.01) | |
| A61B 6/03 | (2006.01) | |
| A61B 6/00 | (2006.01) | |
| G06T 7/00 | (2017.01) | |

(52) U.S. Cl.
CPC ............ *G06T 11/003* (2013.01); *A61B 6/032* (2013.01); *A61B 6/469* (2013.01); *A61B 6/481* (2013.01); *A61B 6/486* (2013.01); *A61B 6/488* (2013.01); *A61B 6/5211* (2013.01); *A61B 6/5217* (2013.01); *A61B 6/541* (2013.01); *A61B 6/545* (2013.01); *G06T 7/0012* (2013.01); *G06T 7/0016* (2013.01); *G06T 7/0081* (2013.01);

(Continued)

(58) Field of Classification Search
None
See application file for complete search history.

(56) References Cited

U.S. PATENT DOCUMENTS 6,845,342 B1 * 1/2005 Basser ............. G01R 33/56341
                                                                                       382/131
7,522,744 B2    4/2009   Bai et al.

(Continued)

FOREIGN PATENT DOCUMENTS

| EP | 0967917 B1 | 11/2005 |
|---|---|---|
| WO | 9832376 A1 | 7/1998 |

(Continued)

*Primary Examiner* — Sean Conner

(57) ABSTRACT

A system of medical imaging including a marking module, a classifying module, a region-of-interest determining module, a curve acquiring module and a delay calculating module. The marking module is used for marking one or more feature regions from pre-scanned images; the classifying module is used for classifying the feature regions by using a classification algorithm model; the region-of-interest determining module is used for selecting a feature region of the same type as a specific diagnostic tissue as a region of interest; the curve acquiring module is used for acquiring a curve of CT values of the region of interest in function of time, based on a relationship between the CT values and scanning time points; the delay calculating module is used for detecting a peak value of the curve and calculating a scan delay time based on a time point corresponding to the peak value.

8 Claims, 3 Drawing Sheets

(52) U.S. Cl.
CPC ............... *G06T 2207/10016* (2013.01); *G06T 2207/10081* (2013.01); *G06T 2207/30104* (2013.01)

(56) References Cited

U.S. PATENT DOCUMENTS

| | | | | |
|---|---|---|---|---|
| 2007/0160312 | A1* | 7/2007 | Blaffert | G06T 7/0024 382/294 |
| 2007/0230653 | A1* | 10/2007 | Okamoto | A61B 5/02007 378/8 |
| 2010/0066756 | A1* | 3/2010 | Yang | A61B 6/481 345/593 |
| 2010/0067767 | A1* | 3/2010 | Arakita | A61B 6/507 382/131 |
| 2011/0150309 | A1* | 6/2011 | Barfett | G06T 7/0028 382/131 |
| 2011/0170759 | A1* | 7/2011 | Bjornerud | G06T 7/0012 382/131 |
| 2011/0190622 | A1* | 8/2011 | Miyoshi | A61B 5/055 600/419 |
| 2013/0259334 | A1* | 10/2013 | Otsuka | G06T 7/0012 382/128 |
| 2013/0274589 | A1* | 10/2013 | Gross | A61B 5/055 600/411 |
| 2014/0003701 | A1* | 1/2014 | Masood | G06T 7/0012 382/134 |

FOREIGN PATENT DOCUMENTS

| | | |
|---|---|---|
| WO | 2009158212 A1 | 12/2009 |
| WO | 2012093364 A1 | 7/2012 |

\* cited by examiner

SYSTEM AND METHOD OF MEDICAL IMAGING

FIELD OF THE INVENTION

The present invention relates to a medical diagnosis field, particularly to a system and a method of medical imaging.

BACKGROUND

In a medical imaging system, such as a computer tomography (CT) and ultrasound, a diagnostic image of a human tissue is usually obtained utilizing a contrast enhancement technique. Taking a CT imaging technique as an example, contrast media is injected into a human blood vessel before scanning, so as to reach to the tissue of interest, e.g., heart, liver and the like, which needs to be diagnosed, along with the blood flow, such that a degree of absorption of the blood vessel for X-rays is obviously different from the other tissues around it, whereby a diagnostic image having an enhanced contrast may be obtained in scanning Usually, scanning is delayed for a period of time after the contrast media is injected, which can obtain a better scanning image. Such delayed time is generally a time from injection of the contrast media to its CT value reaching a peak value. Therefore, for different body tissues, acquisition of an accurate delay time is a key to affect the image quality and even a diagnostic result.

In the prior art, an operator generally injects a little contrast media, and during the process that the contrast media is injected and then enhanced, a pre-scan is performed at a certain time frequency to obtain a plurality of CT images, then regions of interest are drawn in each image manually. By recording CT values of the pixels of the region of interest at a plurality of disperse time points, a curve of CT values in function of time, i.e., HU-Time curve is drawn manually. And by observing the peak value of the curve, it may be determined that the time from injection of the contrast media to the CT value of the region of interest reaching to the peak value is the delay time of the pre-scan, and then a scan delay time in diagnosing may be calculated by a proper formula transformation based on the composition, dosage and the like of the contrast media. In a formal imaging scan diagnose, it may be determined as to when the region of interest is performed a CT scan based on the scan delay time in diagnosing.

The prior art utilizes such a method of manually determining a region of interest, which has a complicated operation and a high time cost, and due to the reasons such as beam hardening artifact, motion artifact and even irregular shape of the region of interest, it is very easy to mark the region of interest in a wrong place. Thus, the obtained HU-Time curve is not accurate enough, and the obtained scan delay time is not accurate, either.

Therefore, there is a need to provide a novel apparatus and method of medical imaging, which can avoid complicated manual operation, reduce the time cost and obtain the region of interest accurately in scanning image, consequently obtaining a more accurate HU-Time curve and a more accurate scan delay time, thus improving the quality of the scanned diagnostic image.

SUMMARY

The exemplary embodiments of the present invention provide a system of medical imaging, comprising a marking module, a classifying module, a region-of-interest determining module, a curve acquiring module and a delay calculating module. The marking module is used for marking one or more feature regions from a plurality of pre-scanned images; the classifying module is used for classifying the feature regions by using a classification algorithm model; the region-of-interest determining module is used for selecting a feature region of the same type as a specific diagnostic tissue as a region of interest; the curve acquiring module is used for acquiring a curve of CT values of the region of interest in function of time, based on a relationship between the CT values of the region of interest in the pre-scanned images and scanning time points of the corresponding images; the delay calculating module is used for detecting a peak value of the curve and calculating a scan delay time based on a time point corresponding to the peak value.

The exemplary embodiments of the present invention also provide a method of medical imaging, comprising the steps of: marking one or more feature regions from a plurality of pre-scanned images; classifying the feature regions by using a classification algorithm model; selecting a feature region of the same type as a specific diagnostic tissue as a region of interest; acquiring a curve of CT values of the region of interest in function of time, based on a relationship between the CT values of the region of interest in the pre-scanned images and scanning time points of the corresponding images; detecting a peak value of the curve, and calculating a scan delay time based on a time point corresponding to the peak value.

Other features and aspects will become apparent from the detailed description, the accompanying drawings and claims that follow.

BRIEF DESCRIPTION OF THE DRAWINGS

The present invention can be understood better in light of the description of exemplary embodiments of the present invention with reference to the accompanying drawings, in which.

DETAILED DESCRIPTION

Hereafter, a detailed description will be given for embodiments of the present invention. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present invention belongs. The terms "first", "second" and the like in the Description and the Claims do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
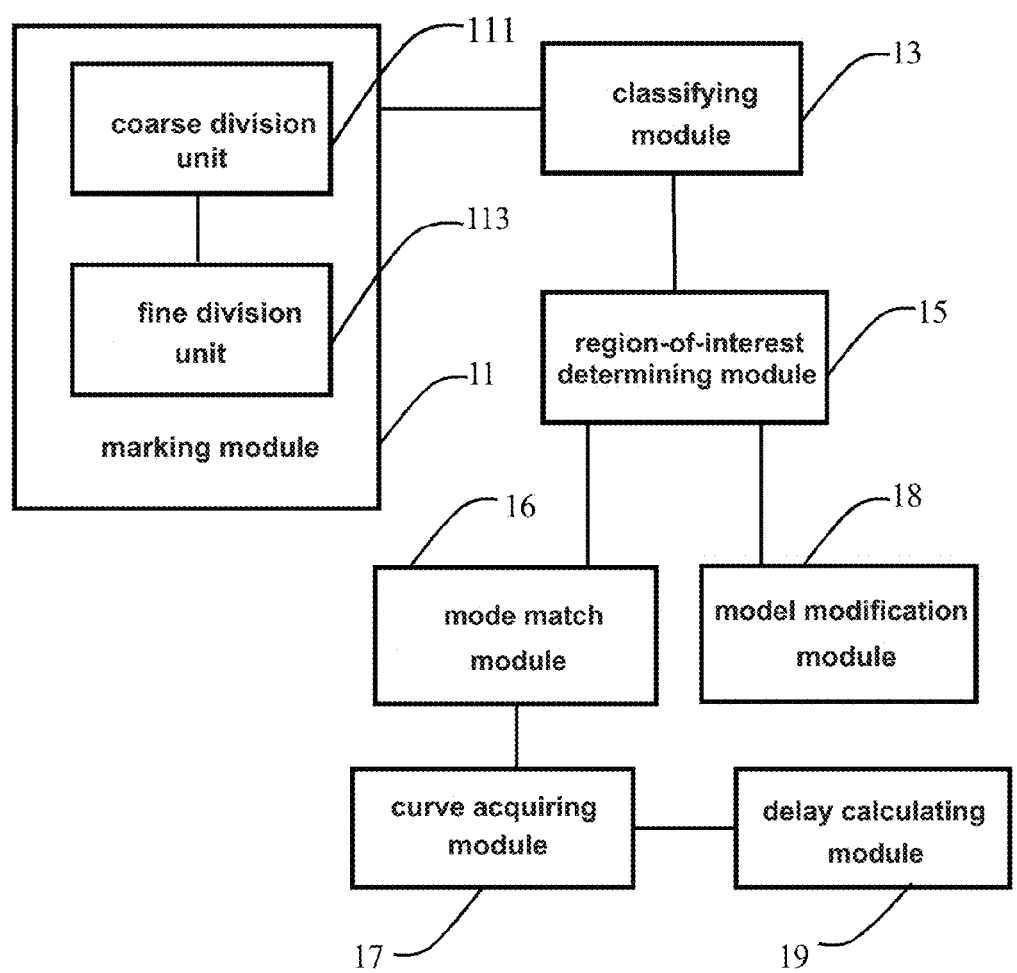
FIG. 1 is a structural block diagram of a system of medical imaging provided by one exemplary embodiment of the present invention.

FIG. 1 is a structural block diagram of a system of medical imaging provided by one exemplary embodiment of the present invention, which may determine a region of interest in the pre-scanned image automatically before contrast enhancement scan diagnose, thus capable of obtaining the scan delay time in diagnosing more accurately, consequently obtaining a diagnostic image with better quality. The above "pre-scan" may refer to, for example, injecting a little contrast media to a patient's blood vessel before performing a formal contrast enhancement scan diagnose on the patient, and then performing a scan on the patient along a time axis, so that a HU-Time curve may be acquired subsequently based on those pre-scanned images that vary in a time sequence, and the scan delay time in contrast enhancement scan diagnose may be calculated.

As shown in FIG. 1, the system of medical imaging comprises a marking module 11, a classifying module 13, a region-of-interest determining module 15, a curve acquiring module 17 and a delay calculating module 19.

The marking module 11 is used for marking one or more feature regions from a plurality of pre-scanned images. The above feature region may refer to, for example, a specific type of human tissues in terms of diagnostic object, e.g., one or more blood vessels; in view of image, the features of the pixels in the feature regions are similar, e.g., being within the same pixel value range or the corresponding CT values being within the same range.

In an embodiment, the marking module 11 may specifically include a coarse division unit 111 and a fine division unit 113. At first, with the use of the coarse division unit, the marking module 11 may judge whether the CT values corresponding to the individual pixels in the pre-scanned image are within a preset range and exclude the pixels whose corresponding CT values are not within the preset range from the feature region, for example, ignore, remove such part of image, or change the values of these pixels into 0, or enhance the contrast between the pixels whose corresponding CT values are within the preset range and the pixels whose corresponding CT values are out of the preset range, etc. The preset range may be set, for example, to be consistent with the range of CT values of the blood vessel.

After the coarse division, with the use of the fine division unit 113, the marking module 11 may further judge whether a degree of linear correlation between the pixels in the pre-scanned image and their surrounding pixels reaches a preset value, and mark the region where degree of linear correlation of the pixels reaches the preset value as one feature region. The above degree of linear correlation may be represented by a correlation coefficient, for example. For instance, after the coarse division, the pixels out of the feature region have been excluded, then one or more separate feature regions, for example, aorta, vein, blood capillary and the like, may be further marked by a fine division.

In other embodiments, the coarse division may also not be made, instead the feature regions are marked by a fine division directly. In addition, image processing technique, e.g., boundary segmentation and the like, may also be employed to mark one or more separate feature region.

Figure 2:
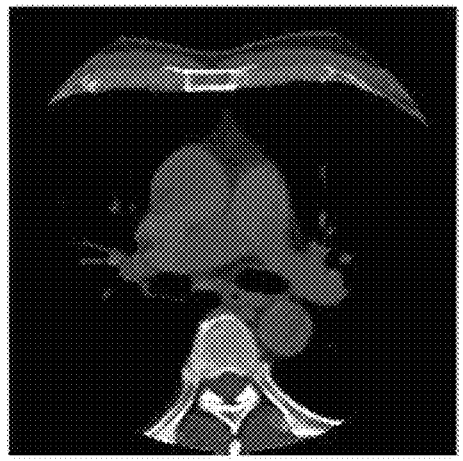
FIG. 2 is one exemplary image obtained by performing a pre-scan of the present invention.
Figure 3:
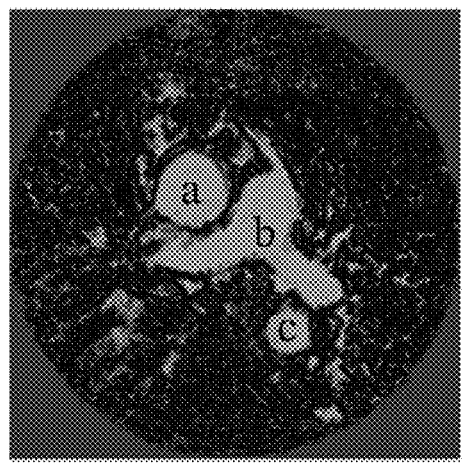
FIG. 3 is an exemplary schematic diagram of marking feature regions in the image as shown in FIG. 2 of the present invention.

FIG. 2 is one exemplary image obtained by performing a pre-scan of the present invention, and FIG. 3 is an exemplary schematic diagram of marking feature regions in the image as shown in FIG. 2 of the present invention. As shown in FIG. 3, the exemplary embodiment of the present invention may mark blood vessel a, blood vessel b, blood vessel c, and some other blood vessels in the image by the above marking module 11.

The classifying module 13 is used to classify the feature regions by using a classification algorithm model. In an embodiment, the classification algorithm model includes K-means classification model or vector space model (VSM). The classifying module 13 uses feature parameters of the marked feature regions (e.g., blood vessels a, b, c) as input values of the K-means classification model or the VSM to acquire the corresponding output values, and classifies the feature regions based on the output values of the K-means classification model or the VSM. For example, the system of medical imaging may pre-store output values of classification models corresponding to various types of blood vessels, and if the blood vessel a matches with the output value corresponding to cardiac artery, then the blood vessel a will be classified to be cardiac artery; if the blood vessel b matches with the output value corresponding to pulmonary artery, the blood vessel b will be classified to be pulmonary artery.

In an embodiment, the above feature parameters comprise one or more of the following parameters:

1, a relationship of CT values of pixels in the feature regions in function of the scanning time points of the plurality of pre-scanned images, i.e., a relationship of CT values in function of time in the HU-Time curve, which may be used as a feature parameter to classify the feature regions because the relationships of CT values corresponding to pixels in different types of feature regions in function of time are different;

2, the number of pixels in the feature regions, which can at least reflect an area of a feature region, and thus may also be used as a feature parameter to classify the feature regions;

3, 1st -Nth moments of pixel values in the feature regions, where N is an integer more than 1, for example, N may be equal to 4, wherein the first moment of the pixel values in the feature regions is a desired value, a second moment is a variance value, a third moment is a skewness value, a fourth moment is a kurtosis value, 1st-Nth moments of pixel values in the feature regions are at least capable of reflecting a shape of a feature region, thus may also be used as a feature parameter to classify the feature regions;

4, centroid of the pixels in the feature regions, which can at least reflect a position of a feature region, and thus may also be used as a feature parameter to classify the feature regions.

The user may make selections among a plurality of feature parameters based on the required precision or a degree of correlation between a feature parameter and a feature region.

The above classification algorithm models are not limited to the listed K-means classification model and VSM, but may also be other algorithm models that can classify different feature regions in images. Moreover, K-means classification model and VSM are both well known classification algorithm models in the prior art, which will not be described in detail.

The region-of-interest determining module 15 is used to select a feature region of the same type as a specific diagnostic tissue as a region of interest. For example, the region-of-interest determining module may judge which type of tissue the present tissue to be diagnosed is based on an instruction received in advance, and seek among all the classified feature regions for a feature region matching with the type of tissue as a region of interest. For instance, before pre-scan, the user may set the location to be diagnosed to be pulmonary artery in the scanning system, then after matching, the region-of-interest determining module automatically determines a feature region b as a region of interest.

Before a formal diagnostic scan, a relationship between CT values of the region of interest in the pre-scanned images and scanning time of the corresponding images may be established, thus obtaining a curve of CT values of the region of interest in function of time, i.e., HU-Time curve, and acquiring a scan delay time by calculating a difference between a time point corresponding to a peak value of the curve and an origin of the time axis. Then when performing a formal imaging scan diagnose, a CT diagnostic scan may be performed at a time after the scan delay time since an injection of contrast media into the blood vessel.

Specifically, the curve acquiring module 17 is used to acquire a curve of CT values of the region of interest in function of time, based on a relationship between the CT values of the region of interest in the pre-scanned images and scanning time points of the corresponding images.

The delay calculating module 49 is used to detect a peak value of the curve and calculating a scan delay time based on a time point corresponding to the peak value, for example, calculating a difference value between a time point corresponding to a peak value of the curve and an origin of the time axis (i.e., a time point when the contrast media is injected before the pre-scan), and performing a proper formula transformation on the difference value based on the effects of the composition, dosage and the like of the contrast media on the scan delay time, so as to obtain the scan delay time.

In an embodiment, the system of medical imaging provided by the exemplary embodiments of the present invention further comprises a mode match module 16 for receiving a diagnostic mode set by an operator and removing a region that does not match with the diagnostic mode from the determined regions of interest based on the diagnostic mode. The above "removing a region that does not match with the diagnostic mode" refers to, re-dividing a part that does not match with the diagnostic mode in the determined region of interest into a non-region-of-interest, so as to reduce the range of the region of interest. For example, before performing a pre-scan, the operator may at first set the diagnostic mode, e.g., selecting which types of blood vessels to be scanned, with respect to a diagnostic purpose and a location to be diagnosed. Taking vein vessel as an example, if the region-of-interest determining module 15 determines a plurality of regions of interest whose types are all the same as the type of vein vessel, and the blood vessels needing to be scanned are the vein vessels near the heart in the diagnostic mode set by the operator, then the mode match module 16 may remove the vein vessels far away from the heart from the determined regions of interest, such that the re-determined regions of interest only include the vein vessel region near the heart. In this way, the accuracy in determining a region of interest may be further increased, so as to be more capable of adapting to the doctor's diagnostic manner.

In an embodiment, the above curve acquiring module 17 may be connected with the region-of-interest determining module 15 directly, so as to acquire a curve of CT values of a region of interest in function of time, and may also be connected with the mode match module 16, so as to acquire a curve of CT values of a region of interest determined after mode matching in function of time.

In an embodiment, the system of medical imaging provided by the exemplary embodiments of the present invention further comprises a model modification module 18 for receiving an invalid feature parameter and inputting the invalid feature parameter into the classification algorithm model to modify the classification algorithm model. For example, one or more feature parameters of a child's artery are distinguished largely from those of an adult's artery, however, the existing classification algorithm models are trained by an adult's feature parameters, therefore, it is potential that a region of interest cannot be determined or a wrong region of interest is determined in a child' scan image, consequently the feature parameters will be invalid. Such condition may also exist between different ethnic groups or between special people and normal people. In this case, by receiving the invalid feature parameters and inputting the invalid feature parameters into the classification algorithm models by the model modification module 18, the classification algorithm models may be re-trained or modified. By modifying a classification algorithm model using a large number of invalid feature parameters, the accuracy and application extent of the classification algorithm model may be increased effectively.

Figure 4:
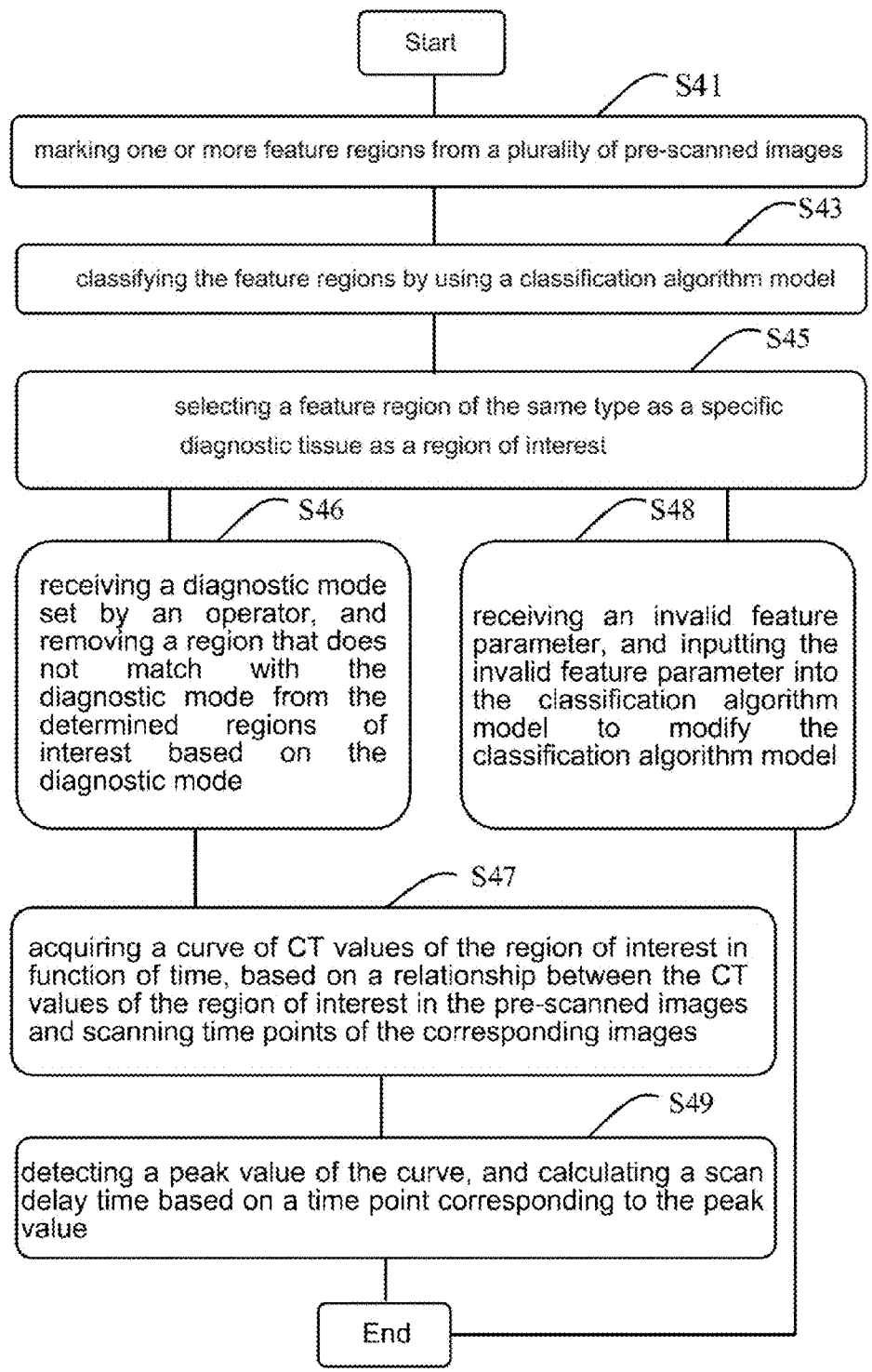
FIG. 4 is a flow chart of a method of medical imaging provided by one exemplary embodiment of the present invention.

FIG. 4 is a flow chart of a method of medical imaging provided by one exemplary embodiment of the present invention, which may be applied into the system of medial imaging provided by the above embodiments, as shown in FIG. 4, the method comprising the following steps:

Step S41: marking one or more feature regions from a plurality of pre-scanned images;

Step S43: classifying the feature regions by using a classification algorithm model;

Step S45: selecting a feature region of the same type as a specific diagnostic tissue as a region of interest;

Step S47: acquiring a curve of CT values of the region of interest in function of time, based on a relationship between the CT values of the region of interest in the pre-scanned images and scanning time points of the corresponding images;

Step S49: detecting a peak value of the curve, and calculating a scan delay time based on a time point corresponding to the peak value.

In an embodiment, Step S43 may include the following steps: using feature parameters of the marked feature regions as input values of the K-means classification model to acquire output values of the K-means classification model, and classifying the feature regions based on the output values of the K-means classification model.

In an embodiment, Step S43 may include the following steps: using feature parameters of the marked feature regions as input values of the K-means classification model or the VSM to acquire output values of the K-means classification model or the VSM, and classifying the feature regions based on the output values of the K-means classification model or the VSM.

In an embodiment, the feature parameters of the feature regions comprise one or more of the following parameters: a relationship between CT values of pixels in the feature regions in function of the scanning time points of the plurality of pre-scanned images, the number of pixels in the feature regions, 1st-Nth moments of the pixel values in the feature regions, and centroid of the pixels in the feature regions, where N is an integer more than 1.

In an embodiment, Step S41 includes the following fine division steps: judging whether a degree of linear correlation between the individual pixels in the pre-scanned images and their surrounding pixels reaches a preset value, and marking the region where degree of linear correlation of the pixels reaches the preset value as one feature region.

In an embodiment, in Step S41, before the fine division steps, the following coarse division steps are further included: judging whether the CT values corresponding to the pixels in the pre-scanned images are within a preset range, and excluding the pixels whose corresponding CT values are out of the preset range from the feature region.

In an embodiment, after Step S45, the following step is included: Step S46: receiving a diagnostic mode set by an operator, and removing a region that does not match with the diagnostic mode from the determined regions of interest based on the diagnostic mode.

In an embodiment, after Step S45, the following step is included: Step S48: receiving an invalid feature parameter, and inputting the invalid feature parameter into the classification algorithm model to modify the classification algorithm model.

In an embodiment, the above Steps S47 and S49 may also be carried out after Step S46.

The operating principles, specific examples and the like of the method of determining based on regions of interest and the method of medical imaging provided by the embodiments of the present invention are consistent with the above region-of-interest determining device and the system of medical imaging, accordingly, detailed description and illustration will not be given.

The system and method of medical imaging provided by the embodiments of the present invention mark feature regions in pre-scanned images by a marking module and classify the marked feature regions so as to judge the types of the feature regions, and select a feature region of the same type as a specific diagnostic tissue as a region of interest, without seeking and drawing feature regions in the images manually, whereby avoiding complicated manual operation, reducing the time cost, and avoiding the problem of multiple errors due to manual operation, which can obtain the regions of interest more accurately, and may in turn help to obtain a more accurate HU-Time curve and a more accurate scan delay time, therefore, the quality of the scanned diagnostic images can be improved.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other embodiments are also falling within the protection scope of the claims.

What is claimed is:

1. A system of medical imaging, comprising:
   a marking module for processing data, wherein the marking module is stored in a memory, marking feature regions from a plurality of pre-scanned images;
   a classifying module for processing data, wherein the classifying module is stored in the memory, classifying the feature regions by using a classification algorithm model wherein the classification algorithm model comprises a K-means classification model or a Vector Space Model (VSM), and the classifying module uses feature parameters of the marked feature regions as input values of the K-means classification model or the VSM to acquire output values of the K-means classification model or the VSM, and classifies the feature regions based on the output values of the K-means classification model or the VSM and wherein the feature parameters of the feature regions comprise the following parameters: a relationship of CT values of pixels in the feature regions as a function of the scanning time points of the plurality of pre-scanned images, the number of pixels in the feature regions, 1st-Nth moments of the pixel values in the feature regions, and centroid of the pixels in the feature regions, where N is an integer more than 1;
   a region-of-interest determining module for processing data, wherein the region-of-interest determining module is stored in the memory, selecting a feature region, among the classified feature regions, of a same type as a specific diagnostic tissue as a region of interest;
   a curve acquiring module for processing data, wherein the curve acquiring module is stored in the memory, acquiring a curve of Computed Tomography (CT) values of the region of interest as a function of time, based on a relationship between the CT values of the region of interest in the plurality of pre-scanned images and scanning time points of the corresponding pre-scanned images; and
   a delay calculating module for processing data, wherein the delay calculating module is stored in the memory:
      detecting a peak value of the curve;
      calculating a scan delay time based on a time point corresponding to the peak value with regard to an origin of a time axis; and
      determining, a transformed scan delay time based on at east one of: a composition, and a dosage of a contrast media.

2. The system of medical imaging according to claim 1, wherein the marking module comprises a fine division unit for judging whether a degree of linear correlation between individual pixels in the pre-scanned images and their surrounding pixels reaches a preset value, and marking a region where the degree of linear correlation of the pixels reaches the preset value as one of said feature regions.

3. The system of medical imaging according to claim 1, further comprising a mode match module for receiving a diagnostic mode set by an operator and removing a region not matching with the diagnostic mode from the determined regions of interest based on the diagnostic mode, wherein the mode match module is stored in the memory.

4. The system of medical imaging according to claim 1, further comprising a model modification module for receiving an invalid feature parameter and inputting the invalid feature parameter into the classification algorithm model to modify the classification algorithm model, wherein the model modification module is stored in the memory.

5. A method of medical imaging, comprising:
marking feature regions from a plurality of pre-scanned images;
classifying the feature regions by using a classification algorithm model; wherein the classification algorithm model comprises a K-means classification model or a Vector Space Model (VSM), said classifying the feature regions by using a classification algorithm model comprising:
using feature parameters of the marked feature regions as input values of the K-means classification model or the VSM to acquire output values of the K-means classification model or the VSM, and classifying the feature regions based on the output values of the K-means classification model or the VSM and wherein the feature parameters of the feature regions comprise the following parameters: a relationship of CT values of pixels in the feature regions as a function of the scanning time points of the plurality of pre-scanned images, the number of pixels in the feature regions, 1st-Nth moments of the pixel values in the feature regions, and centroid of the pixels in the feature regions, where N is an integer more than 1;
selecting a feature region, among the classified feature regions, of a same type as a specific diagnostic tissue as a region of interest;
acquiring a curve of Computed Tomography (CT) values of the region of interest as a function of time, based on a relationship between the CT values of the region of interest in the pre-scanned images and scanning time points of the corresponding pre-scanned images;
detecting a peak value of the curve;
calculating a scan delay time based on a time point corresponding to the peak value with regard to an origin of a time axis; and
determining a transformed scan delay time based on at least one of: a composition, and a dosage of a contrast media.

6. The method of medical imaging according to claim 5, wherein said marking feature regions from a plurality of pre-scanned images comprises fine division steps comprising:
judging whether a degree of linear correlation between pixels in the pre-scanned images and their surrounding pixels reaches a preset value; and
marking a region where degree of linear correlation of the pixels reaches the preset value as one of said feature regions.

7. The method of medical imaging according to claim 5, further comprising, after said selecting a feature region of the same type as a specific diagnostic tissue as a region of interest, receiving a diagnostic mode set by an operator, and removing a region not matching with the diagnostic mode from the determined regions of interest based on the diagnostic mode.

8. The method of medical imaging according to claim 5, further comprising, after said selecting a feature region of the same type as a specific diagnostic tissue as a region of interest, receiving an invalid feature parameter, and inputting the invalid feature parameter into the classification algorithm model to modify the classification algorithm model.

* * * * *